US010155012B2

(12) United States Patent
Ishii et al.

(10) Patent No.: US 10,155,012 B2
(45) Date of Patent: Dec. 18, 2018

(54) CATECHOLAMINE PRODUCTION ACCELERATOR, AND THERAPEUTIC AND PREVENTIVE AGENT AND THERAPEUTIC AND PREVENTIVE FOOD COMPOSITION FOR DISEASES CAUSED BY CATECHOLAMINE DEFICIENCY

(71) Applicant: WELL STONE CO., Miyazaki (JP)

(72) Inventors: Yoichi Ishii, Miyazaki (JP); Takayuki Nemoto, Miyazaki (JP); Takeshi Okamoto, Miyazaki (JP)

(73) Assignee: WELL STONE CO., Miyazaki (JP)

( * ) Notice: Subject to any disclaimer, the term of this patent is extended or adjusted under 35 U.S.C. 154(b) by 45 days.

(21) Appl. No.: 15/107,546

(22) PCT Filed: Jan. 13, 2015

(86) PCT No.: PCT/JP2015/050586
§ 371 (c)(1),
(2) Date: Jun. 23, 2016

(87) PCT Pub. No.: WO2015/108014
PCT Pub. Date: Jul. 23, 2015

(65) Prior Publication Data
US 2016/0317587 A1 Nov. 3, 2016

(30) Foreign Application Priority Data
Jan. 20, 2014 (JP) ................. 2014-007845

(51) Int. Cl.
| A61K 35/62 | (2006.01) |
| A23J 3/04 | (2006.01) |
| A61K 9/00 | (2006.01) |
| A61K 9/14 | (2006.01) |
| A23L 33/10 | (2016.01) |

(52) U.S. Cl.
CPC .......... *A61K 35/62* (2013.01); *A23J 3/04* (2013.01); *A23L 33/10* (2016.08); *A61K 9/0053* (2013.01); *A61K 9/148* (2013.01)

(58) Field of Classification Search
CPC ............................. A61K 36/00; A61K 35/62
See application file for complete search history.

(56) References Cited

U.S. PATENT DOCUMENTS

| 2011/0086106 A1 | 4/2011 | Ishii et al. |
| 2012/0294950 A1 | 11/2012 | Ishii |

FOREIGN PATENT DOCUMENTS

| CN | 1386511 A | * 12/2002 |
| CN | 102675468 | 9/2012 |
| JP | 59-216572 | 12/1984 |
| JP | 63-238009 | 10/1988 |
| JP | 2-215723 | 8/1990 |
| JP | 2-215725 | 8/1990 |
| JP | 2-215726 | 8/1990 |
| JP | 10-2591256 | 9/1998 |
| JP | 2008-81476 | 4/2008 |
| JP | 2013-32308 | 2/2013 |
| KR | 101198192 | 11/2012 |
| RU | 2438681 C1 | 1/2012 |
| WO | 2006/082609 | 8/2006 |

OTHER PUBLICATIONS

Rude, Monoamine-containing neurons in the nerve cord and body wall of Lumbricus terrestris. J Comp Neurol, (1966) vol. 128, No. 3, pp. 397-412.*
Wanda J. Krall et al., "Cholinesterase Inhibitors: A Therapeutic Strategy for Alzheimer Disease", The Annals of Pharmacotherapy, 1999, 33(4), pp. 441-450.
Mahito Kimura, Igaku no Ayumi, "Pharmacological treatment of Alzheimer's disease", Journal of Clinical and Experimental Medicine, 2011, 236(10), pp. 980-985, partial English translation.
International Search Report dated Mar. 17, 2015 in International Application No. PCT/JP2015/050586.
Beverly M. Francis et al., "Reduced Tissue Levels of Noradrenaline Are Associated with Behavioral Phenotypes of the TgCRND8 Mouse Model of Alzheimer's Disease", Neuropsychopharmacolgoy (2012) 37: 1934-1944.
Patricia Szot, "Common factors among Alzheimer's disease, Parkinson's disease, and epilepsy: Possible role of the noradrenergic nervous system", Epilepsia (2012) 53 (Suppl. 1): 61-66.
Yunqi Xu et al., "Neurotransmitter receptors and cognitive dysfunction in Alzheimer's disease and Parkinson's disease", Progress in Neurobiology (2012) 97: 1-13.
Ian H. Robertson, "A noradrenergic theory of cognitive reserve: implications for Alzheimer's disease", Neurobiology of Aging (2013) 34: 298-308.
Shuko Takeda et al., "Koketsuatsu to Alzheimer-gata Ninchisho", Journal of Blood Pressure, 2007, 14(5), 165-169 (with machine translation of Abstract part).
Tomohiro Umeda et al., "Hypercholesterolemia accelerates intraneuronal accumulation of Aβ oligomers resulting in memory impairment in Alzheimer's disease model mice", Life Sciences, 2012, 91, 1169-76.
Shuko Takeda et al., "Mechanistic Interaction Between Diabetes Mellitus and Alzheimer Disease", Journal of Japan Society for the Study of Obesity, 2010, 16(3), 192-195 (with machine translation of "Introduction").

(Continued)

Primary Examiner — Qiuwen Mi
(74) Attorney, Agent, or Firm — Wenderoth, Lind & Ponack, L.L.P.

(57) ABSTRACT

An object of the present invention is to provide: a catecholamine production accelerator comprising a natural product as an active ingredient; a therapeutic agent and preventive agent for diseases caused by catecholamine deficiency; and food compositions for the treatment or prevention of diseases caused by catecholamine deficiency. Provided are: a catecholamine production accelerator comprising a dry powder, ground product and/or extract of an earthworm as an active ingredient; a therapeutic agent and preventive agent for a disease caused by catecholamine deficiency; and loud compositions for the treatment or prevention of a disease caused by catecholamine deficiency. It is preferred that the disease caused by catecholamine deficiency be selected from the group consisting of Alzheimer's disease and Parkinson's disease.

6 Claims, 3 Drawing Sheets

(56) References Cited

OTHER PUBLICATIONS

Takashi Abe et al., "Chiho Mikata to Chiryo Kanri no Shindan Chiho Kanja ni Okeru Shinkei Dentatsu Busshitsu no Henka", Modern Physician, 1988, 18(4), 367-373 (with machine translation of Abstract part).

Akiko Ikeda, "Stress Shakai o Kangaeru Utsubyo to Do Mukiauka", Chemistry & chemical industry, 2007, 60(10), 971-975 (With machine translation of p. 972, right col., 3rd to 4th paragraph).

Yuhao Ren, et al. "Relevant activities of extracts and constituents of animals used in traditional Chinese medicine for central nervous system effects associated with Alzheimer's disease", Journal of Pharmacy and Pharmacology, 2006, 58(7), 989-96.

Extended European Search Report dated Aug. 1, 2017 in corresponding European Application No. 15737735.9.

Kim et al., "Neurotropic and neuroprotective activities of the earthworm peptide Lumbricusin", Biochemical and Biophysical Research Communications, 2014, vol. 448, No. 3, pp. 292-297.

Database WPI, Week 201315, Thomson Scientific, London, GB; AN 2012-R31743, XP002772217.

\* cited by examiner

CATECHOLAMINE PRODUCTION ACCELERATOR, AND THERAPEUTIC AND PREVENTIVE AGENT AND THERAPEUTIC AND PREVENTIVE FOOD COMPOSITION FOR DISEASES CAUSED BY CATECHOLAMINE DEFICIENCY

TECHNICAL FIELD

The present invention relates to: a catecholamine production accelerator; a therapeutic agent and preventive agent for a disease caused by catecholamine deficiency; and food compositions for the treatment or prevention of a disease caused by catecholamine deficiency.

BACKGROUND ART

Catecholamines are compounds having a catechol and an amine and exist in vivo as a part of neurotransmitters. The most abundant catecholamines in vivo are adrenaline, noradrenaline and dopamine, and these are derived from tyrosine. Tyrosine is converted into L-DOPA (L-3,4-dihydroxyphenylalanine), which is further converted into dopamine. Noradrenaline is converted from dopamine, and adrenaline is converted from noradrenaline.

Catecholamine deficiency has been confirmed in neurodegenerative diseases such as Alzheimer's disease and Parkinson's disease, and prevention and treatment by promotion of catecholamine production have been put into practice and studied. For instance, as anti-Parkinson's disease agents, adrenaline, noradrenaline and dopamine precursors such as phenylalanine, tyrosine and L-DOPA are administered. In addition, for the prevention of metabolism induced by oxidative removal of amino groups by monoamine oxidase, monoamine oxidase inhibitors have been used as anti-Parkinson's disease agents. For Alzheimer's disease, drug therapy has been mainly employed in recent years; however, no fundamental therapeutic agent is yet to be found at the present. Nevertheless, the importance of noradrenaline and dopamine has been examined and reports have been made on the reduction in the tissue concentration of noradrenaline observed in Alzheimer's disease model mice (Non-patent Documents 1 to 4) therefore, a preventive or therapeutic method for Alzheimer's disease by promotion of catecholamine production is expected to be developed.

Meanwhile, mainly in the Oriental countries, earthworm extracts and dry earthworm powders have been used since ancient times as preventive agents and therapeutic agents for various diseases, and examples of their use that have been known include bladder stone-reducing agents, bladder stone excretion-promoting agents, therapeutic agents for jaundice, oxytocics, tonic agents, hair growth agents, aphrodisiacs, antipyretics, therapeutic agents fir convulsion, blood circulation promoters, therapeutic agents for hemiplegia, indirect analgesics, diuretics, antiasthmatics and antihypertensive agents.

However, no report has even been made on a catecholamine production accelerator that contains an earthworm as an active ingredient or the utilization of an earthworm in the prevention and therapy of Alzheimer's disease and Parkinson's disease.

RELATED ART DOCUMENTS

Non-Patent Documents

Non-patent Document 1: Francis B M et al., Neuropsychopharmacology (2012) 37:1934-1944

Non-patent Document 2: Szot P, Epilepsia (2012) 53 (Suppl.1):61-66

Non-patent Document 3: Xu Y et al., Progress in Neurobiology (2012) 97:1-13

Non-patent Document 4: Robertson I H, Neurobiology of Aging (2013) 34:298-308

SUMMARY OF THE INVENTION

Problems to be Solved by the Invention

The therapy of neurodegenerative diseases such as Alzheimer's disease and Parkinson's disease is believed to involve drug administration over a long time; therefore, a drug that is safe and has little side effects is particularly necessary, and there is thus a demand for a catecholamine production accelerator as well as a preventive and therapeutic agent for Alzheimer's disease and Parkinson's disease that are derived from a natural product.

In view of the above, an object of the present invention is to provide: a catecholamine production accelerator comprising a natural product as all active ingredient a preventive and therapeutic agent for diseases caused by catecholamine deficiency; as well as a food composition and pharmaceutical composition for improvement of the symptoms of diseases caused by catecholamine deficiency.

Means for Solving the Problems

That is, the catecholamine production accelerator according to the present invention is characterized by comprising a dry powder, ground product and/or extract of an earthworm as an active ingredient.

The therapeutic agent or preventive agent for a disease caused by catecholamine deficiency according to the present invention is characterized by comprising the above-described catecholamine production accelerator.

The therapeutic or preventive food composition for a disease caused by catecholamine deficiency according to the present invention is characterized by comprising the above-described catecholamine production accelerator.

In the therapeutic agent or preventive agent for a disease caused by catecholamine deficiency according to the present invention, it is preferred that the disease caused by catecholamine deficiency be selected from the group consisting of Alzheimer's disease and Parkinson's disease.

In the therapeutic or preventive food composition for a disease caused by catecholamine deficiency according to the present invention, it is preferred that the disease caused by catecholamine deficiency be selected from the group consisting of Alzheimer's disease and Parkinson's disease.

The method of producing a catecholamine production accelerator according to the present invention is characterized by comprising the use of a dry powder, ground product or extract of an earthworm.

The method of producing a therapeutic agent or preventive agent for a disease caused by catecholamine deficiency according to the present invention is characterized by comprising the use of a dry powder, ground product or extract of an earthworm.

The method of producing a therapeutic or preventive food composition for a disease caused by catecholamine deficiency according to the present invention is characterized by comprising the use of a dry powder, ground product or extract of an earthworm.

The method of promoting the catecholamine production according to the present invention is characterized by comprising: the use of a dry powder, ground product and/or extract of an earthworm.

The dry powder, ground product or extract of an earthworm according to the present invention is for the use in the treatment of a disease caused by catecholamine deficiency.

The method of treating or preventing a disease caused by catecholamine deficiency according to the present invention is characterized by comprising administration of a dry powder, ground product and/or extract of an earthworm to a subject in an effective dose.

Effects of the Invention

According to the present invention, a catecholamine production accelerator comprising a natural product as an active ingredient, a preventive and therapeutic agent for diseases caused by catecholamine deficiency, as well as a food composition and pharmaceutical composition for improvement of the symptoms of diseases caused by catecholamine deficiency can be provided.

MODE FOR CARRYING OUT THE INVENTION

In the present invention, the earthworm used as a raw material is not particularly restricted, and examples of earthworm that can be used include *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima sieboldi* Horst, *Pheretima hilgendorfi, Pontodrilus matsushimensis* lizuka, *Tubifex hattai* Nomura, *Limnodrilus gotoi* Hatai (=*L. Socialis* Stephenson).

In the present invention, the term "dry powder" of an earthworm means a powder obtained by drying a ground product or extract of an untreated or pretreated earthworm. The term "ground product" of an earthworm means an untreated or pretreated earthworm ground into a liquid or paste form. The term "extract" of an earthworm means an extract obtained by dissolving an untreated or pretreated earthworm or a ground product thereof in water, an aqueous solution or an organic solvent and subsequently removing or separating insoluble fractions. The pretreatment is not particularly restricted, and examples thereof include the below-described treatment for removal of dirt and the like. Further, the dry powder, ground product and extract of an earthworm may also be subjected to a post-treatment, examples of which include granulation, filtration, purification, concentration, dilution and pH adjustment.

The grinding method for obtaining a ground product of an earthworm is not particularly restricted and grinding can be performed using, for example, a homogenizer, a blender, a homomixer, a grinder or a high-pressure cell crushing apparatus.

The extraction method for obtaining an extract of an earthworm is not particularly restricted and extraction can be performed by, for example, dissolving a dry powder or ground product of the earthworm in an extraction solvent and subsequently removing or separating insoluble fractions. Examples of the extraction solvent include water, aqueous solutions, and organic solvents such as ethanol, acetone and ethyl acetate. These extraction solvents may be used individually, or two or more thereof may be used in combination. Thereamong, water, ethanol or an aqueous ethanol solution is preferably used.

The drying method liar obtaining a dried product of an earthworm is not particularly restricted and drying can be performed by a drying method such as freeze-drying, heat-drying or spray-drying. Thereamong, freeze-drying is preferred for the below-described reasons.

In the present invention, the dry powder, ground product or extract of the earthworm can be incorporated in an effective amount in accordance with the purpose thereof. The appropriate amount depends on a variety of factors such as the intended purpose, the route and mode of administration and the production method of the dry powder or the like of the earthworm; however, for the purpose of preventing diseases caused by catecholamine deficiency or treating a mild disease, the appropriate amount is preferably to 15,000 mg/day, more preferably 12 to 1,800 mg/day, still more preferably 120 to 180 mg/day, in terms of the weight of the thy powder of the earthworm obtained b removing the digested matters remaining in the digestive tract of the earthworm as well as the dirt and the like adhering to the skin of the earthworm as described below, grinding the earthworm and then freeze-drying the resulting ground product. Further, for the purpose of treating a severe disease caused by catecholamine deficiency, the appropriate amount is preferably 1 to 15,000 mg/day, more preferably 18 to 3,600 mg/day, still more preferably 180 to 360 mg/day.

The forms of the catecholamine production accelerator, therapeutic agent, preventive agent and food composition at the present invention are not particularly restricted and can be any of a solid form, a powder form, a semisolid form and a liquid form.

In the present invention, the dry powder, ground product or extract of the earthworm can be used as is. Alternatively, particularly the catecholamine production accelerator, therapeutic agent and preventive agent of the present invention may contain a pharmaceutically acceptable carrier and can be administered orally or parenterally (e.g., intravenous administration or direct administration to the affected site in the form of a tablet, granule, powder, capsule, soft capsule, liquid, injectable, suppository or sustained release agent or the like. As the pharmaceutically acceptable carrier, for example, an excipient, is binding agent, a disintegrant, a fluidizing agent, a lubricant, a coating agent, a suspending agent, a colorant, a sweetening agent or a surfactant can be used, and the resultant can be made into the form of an ordinary pharmaceutical preparation in accordance with a known method. Further, other therapeutic and prophylactic component(s) and pharmaceutically acceptable additive(s) may also be incorporated.

In the present invention, particularly in the catecholamine production accelerator and food composition of the present invention, an additive(s) usually used in food products may also be incorporated. Examples of additives that can be used include excipients, binding agents, disintegrants, fluidizing agents, lubricants, coating agents, suspending agents, colorants, sweetening agents and surfactants, and the resultant can be made into the form of an ordinary food composition in accordance with a known method. Further, other food product(s) or food-derived component(s) may be incorporated as well.

In the present invention, among dry powders, ground products and extracts of earthworms, from the standpoint of the storage stability in the production process, it is preferred to use a dry powder of an earthworm. The dry powder of the earthworm may be dissolved and/or dispersed in a liquid such as water in advance and the resultant may be subsequently mixed with other component(s), examples of which include conventional carriers and additives that are used pharmaceutically and/or in food products.

In the present invention, the disease caused by catecholamine deficiency is not particularly restricted, and it is preferably selected from the group consisting of Alzheimer's disease and Parkinson's disease.

For oral administration of an earthworm as a raw material, it is preferred to remove the digested matters remaining in the digestive tract of the earthworm, the dirt adhering to the skin and the like. In the present invention, the method for such removal is not particularly restricted and the removal can be performed by a known method. For example, a method of allowing a live earthworm to excrete yellow soil contained in the digestive tract by immersing the earthworm into an aqueous solution of an alkali salt such as a sodium salt or a potassium salt (a method described in Japanese Unexamined Patent Application Publication Nos. H1-47718, H1-47719, H1-47720 and H1-268639) or a method of removing castings from the digestive tract of a live earthworm by leaving the earthworm in an aqueous acid solution maintained at 6 to 26° C. for 0.1 to 5 hours (a method described in Japanese Unexamined Patent Application Publication No. H3-72427) can be employed.

In the present invention, as a removal method, it is preferred to bring the earthworm into contact with the below-described metal chloride and/or hydroxycarboxylic acid.

The metal chloride is a chloride of at least one metal selected from the group consisting of potassium, sodium, magnesium and calcium. That is, the metal chloride is at least one selected from the group consisting of potassium chloride, sodium chloride, magnesium chloride and calcium chloride. Further, the metal chloride may also be a mixture of these metal chlorides, or a mixture of one or more of these metal chlorides and other harmless component(s) that can be added to food products. Examples of such mixtures include dietary salts, rock salts and bay salts. The metal chloride can be used by sprinkling it in a powder form over a live earthworm and this causes a contact between the earthworm and the metal chloride.

After allowing the metal chloride to come into contact with the live earthworm, it is preferred to bring the live earthworm into contact with a hydroxycarboxylic acid in the below-described manner. Alternatively, the earthworm may be brought into contact with a hydroxycarboxylic acid in the below-described manner without a preceding contact with the metal chloride.

The contact with the hydroxycarboxylic acid can also be made by sprinkling the hydroxycarboxylic acid in a powder form over the live earthworm. Alternatively, the live earthworm may be immersed in an aqueous solution of the hydroxycarboxylic acid that has a pH of 2 to 5. In cases where the contact with the hydroxycarboxylic acid is made after a contact with the metal chloride, it is preferred that the contact with the hydroxycarboxylic acid be made promptly after the contact with the metal chloride. It is also preferred that the earthworm be washed with water before being brought into contact with the hydroxycarboxylic acid. By removing the metal chloride by washing with water and then bringing the earthworm into contact with the hydroxycarboxylic acid, a dry earthworm powder having a high enzyme activity can be obtained. When the earthworm is washed with water before the contact with the hydroxycarboxylic acid, the washing of the earthworm with water is performed preferably within 30 minutes, more preferably within 20 minutes, after the initiation of the contact with the metal chloride. The method of washing the earthworm with water is not particularly restricted, and a known method can be employed.

If live earthworms are left in contact with hydroxycarboxylic acid powder for a long time, the earthworms are killed, so that their vital functions are lost and the digested matters in their digestive tracts are no longer excreted. Therefore, it is preferred to dilute the hydroxycarboxylic acid with water as soon as possible, preferably within 30 seconds, more preferably within 20 seconds, so as to adjust the pH to a range of 2 to 5.

Since a hydroxycarboxylic acid creates a living environment unpleasant to earthworms, live earthworms, following their self-preservation instinct, try to improve the living environment through discharge of body fluids and excretion. Further, since hydroxycarboxylic acids have disinfecting properties, they are expected not only to play a role in promoting excretion of digested matters and the like remaining in the digestive tract as described above, but also to have an effect of killing bacteria adhering to the earthworms.

In the above-described method, any crystalline hydroxycarboxylic acid can be used regardless of the number of its hydroxy groups and carboxyl groups, as long as it assumes a crystalline form under the conditions of its use. That is, the crystalline hydroxycarboxylic acid may be any of monohydroxy monocarboxylic acids, monohydroxy polycarboxylic acids, polyhydroxy monocarboxylic acids and polyhydroxy polycarboxylic acids.

Examples of the hydroxycarboxylic acid used in the present invention include glycolic acid, lactic acid, acetic acid, β-hydroxypropionic acid, α-hydroxy-n-butyric acid, β-hydroxy-n-butyric acid, α-hydroxy-n-valeric acid, β-hydroxy-n-valeric acid, malic acid, α-methylmalic acid, α-hydroxyglutaric acid, β-hydroxyglutaric acid, citric acid, malonic acid and succinic acid. Thereamong, lactic acid, acetic acid, malic acid, citric acid, malonic acid and succinic acid are preferred because they can be used in food products and easily obtained. The above-described hydroxycarboxylic acids may be used individually, or two or more thereof may be used in combination.

Water constitutes 65% of the tissues of as live earthworm. Although the self-preservation functions of a live earthworm remain, effective for a certain time, the death of the live earthworm results in the onset of enzyme activities; therefore, it is required to carefully control the time in which the live earthworm is placed under an unpleasant living environment. The length of this time varies depending on the conditions; however, it is usually in a range of 3 to 180 minutes.

It is preferred that the thus hydroxycarboxylic acid-treated live earthworm be washed with water and then ground into a liquid-form or paste-form ground product. The washing is preferably performed with pure water. The washing method is not particularly restricted, and a known washing method with water can be employed. The total time of the treatment process before the grinding, that is, the duration of the period from the sprinkling of the metal chloride on the live earthworm to the completion of the removal of the hydroxycarboxylic acid by washing with water, is preferably not longer than 240 minutes.

The grinding method is not particularly restricted and, for example, the grinding is usually performed at 1 to 25° C. using a homogenizer, a blender, a homomixer, a grinder, a high-pressure cell-crushing apparatus or the like. From the standpoint of inhibiting degradation of the earthworm components, it is preferred that the grinding be performed at a low temperature, more preferably at a temperature of 2 to 15° C.

The ground product obtained by grinding the earthworm is placed on a stainless-steel tray or the like and subjected to freeze-drying. In this process, a decomposition gas may be generated because the enzymes contained in the living body of the earthworm are inactive in the living cells but act instantaneously on dead cells. In order to inhibit the generation of a decomposition gas, it is preferred that, before being freeze-dried, the ground product be momentarily cooled rapidly and frozen at −18° C. to −35° C. so as to suppress the enzyme actions.

In this manner, for the preparation of earthworm powder without impairing the inherent pharmacological actions of the earthworm, it is preferred that the ground earthworm be quickly frozen. On the other hand, an excessively rapid freezing is not preferred because when the ground earthworm is frozen in an excessively short period of time, the impurities existing together with the proteins that are major components of an earthworm paste can form spots of unfrozen parts and thus may not be separated. Therefore, the freezing is performed at a low temperature of −18° C. to −35° C. over a period of preferably 20 to 240 hours, more preferably 50 to 170 hours.

For the freeze-drying, it is important to select conditions that allow removal of water as well as impurities without leaving any impurity. Accordingly, it is preferred that the freeze-drying be performed under a pressure of 50 Pa or less while increasing the temperature stepwise in a range of −60'C to +90° C. over a period of 10 to 60 hours.

As a freeze-drying method, for example, as described above, after freezing the ground product at a temperature of −18° C. to −35° C. over a period of 20 to 240 hours, the resultant is vacuum freeze-dried over a period of 10 to 60 hours while increasing the temperature in several steps in a range of −60° C. to +90° C. and reducing the pressure in several steps in a range of 25 to 40 Pa, thereby a sterile pale yellow dry earthworm powder can be obtained.

Further, it is also preferred to incorporate the steps of dissolving the thus freeze-dried ground product in water or an aqueous ethanol solution; and removing or separating insoluble fractions. The step of removing or separating insoluble fractions can be performed in the same manner as described above and comprises precipitation carried out by leaving the resulting solution to stand, centrifugation, filtration and the like. The step of dissolving the freeze-dried ground product in water or an aqueous ethanol solution is preferably performed with stirring or shaking. The time required for dissolution of the freeze-dried ground product in water is preferably 1 to 120 minutes, more preferably 5 to 80 minutes. The ethanol concentration of the aqueous ethanol solution is not particularly restricted; however, it is preferably 10 to 70% (v/v), more preferably 30 to 60%.

As the catecholamine production accelerator, therapeutic agent, preventive agent and food composition of the present invention, a supernatant obtained, from water or aqueous ethanol solution in which freeze-dried ground earthworm is dissolved as described above may be used as is in the state of an aqueous solution, or may be used at the form of a concentrate after evaporating water therefrom. The supernatant may also be dried to be used in a powder form, and the powder obtained by drying the supernatant may be dissolved in water for use. Further, powder obtained by freeze-drying an earthworm paste can be used as is, without being dissolved in water or an aqueous ethanol solution.

Further, in the present invention, as a removal method, before the treatment of placing live earthworms under an unpleasant environment, that is, before bringing live earthworms into contact with a metal chloride or a hydroxycarboxylic acid as described above, it is preferred that the live earthworms be transferred to a flat box such as a bread box and left to stand for 10 to 50 hours in a bright place, followed by removal of dirt adhering to the earthworm skin. The duration of leaving the live earthworms in a bright place is more preferably 12 to 24 hours. In this process, it is preferred that the amount of the live earthworms contained in the flat box be such an amount that the earthworms are piled up to a thickness of 30 to 60 mm, preferably 40 to 50 mm. Care should be taken so that the flat box contains no foreign matter such as sand or mud and, since earthworms are nocturnal and thus become active in their living activities in dark place and this may lead to their physical exhaustion, it is preferred to employ a light culture method or the like during the night so as to keep the flat box under a bright condition. This treatment makes the live earthworms exhibit their self-protection instinct and try to maintain their living environment by excreting the digested matters remaining in their digestive tracts, covering their entire body with the excrements and thereby preventing evaporation of water. Thus, by repeatedly striping off this covering dirt, namely excrements, by an appropriate means, the digested matters in the digestive tracts of the earthworms and the dirt adhering to their skin can be eventually removed.

The dirt adhering to the earthworms skin can be stripped off by, for example, covering the live earthworms with a nonwoven fabric and allowing the dirt to adsorb to the fabric. By performing this process of leaving the earthworms in a bright place and removing the dirt adhering to their skin in combination with the above-described process of bringing the earthworms into contact with the a metal chloride and/or a hydroxycarboxylic acid, further excretion and removal of toxic matters contained the earthworms' body can be expected.

In the present invention, as a method for obtaining a dry earthworm powder, the following methods are preferred particularly from the standpoint of the storage stability of the resulting dry powder.

(A-1) A method of producing a dry earthworm powder, the method comprising the steps of:

bringing a live earthworm into contact with a chloride of at least one metal selected from the group consisting of potassium, sodium, magnesium and calcium; and subsequently bringing the live earthworm into contact with as powder-form hydroxycarboxylic acid, diluting the resultant with water to adjust the pH to 2 to 5, maintaining the resulting dilution for 3 to 180 minutes, washing the live earthworm with water, grinding the live earthworm and then freeze-drying the thus obtained ground product.

(A-2) A method of producing a dry earthworm powder, the method comprising the steps of:

bringing a live earthworm into contact with a chloride(s) of a metal(s) selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water, grinding the live earthworm and then freeze-drying the thus obtained ground product.

(A-3) The method of producing a dry earthworm powder according to the above-described (A-1) or (A-2), which further comprises the steps of; dissolving the thus freeze-dried ground product into water of an aqueous ethanol solution; removing or separating insoluble fractions; and then further freeze-drying the resultant.

Further, after the freeze-drying of the ground product obtained by grinding the live earthworm, from the standpoint of sterilization of the resulting dried product, the dried product is preferably heat-treated at a temperature of 110° C. or higher but lower than 130° C. When the heating temperature is lower than 110° C., the dried product may not be sterilized sufficiently, whereas when the heating temperature is 130° C. or higher, the enzymes contained in the dried earthworm product are inactivated and their activities are thus reduced, which is not preferred. The heating temperature is more preferably 115 to 125° C. The heating method is not particularly restricted., and examples thereof include a method of blowing hot air; a method using a heating jacket; as method of heating the subject on a tray or the like using a heater; and a method using a thermostat incubator. The heating time is preferably 30 seconds to 130 minutes, more preferably 30 minutes to 90 minutes, still more preferably 60 minutes to 90 minutes. An excessively short heating time may result in insufficient sterilization while an excessively long heating time may cause the loss of enzyme activities, neither of which is preferred. When enzymes contained in a liquid are subjected to the above-described heat treatment, the activities of the enzymes are lost; therefore, in the present invention, it is preferred to use a dry earthworm powder.

In the present invention, as a method for obtaining a ground product of an earthworm, the following methods are preferred.

(B-1) A method of producing a ground product of an earthworm, the method. comprising the steps of:

bringing a live earthworm into contact with a chloride of at least one metal selected from the group consisting of potassium, sodium, magnesium and calcium; and subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water and then grinding the live earthworm.

(B-2) A method of producing a ground product of an earthworm, the method comprising the steps of:

bringing a live earthworm into contact with a chloride(s) of a metals) selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water and then grinding the live earthworm.

In the present invention, as a method for obtaining an earthworm extract, the following methods are preferred.

(C-1) A method of producing an earthworm extract, the method comprising the steps of:

bringing a live earthworm into contact with a chloride of at least one metal selected from the group consisting of potassium, sodium, magnesium and calcium; and subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water, grinding the live earthworm, freeze-drying the resulting ground product, dissolving the thus freeze-dried product in water or an aqueous ethanol solution, and then removing or separating insoluble fractions.

(C-2) A method of producing an earthworm extract; the method comprising the steps of:

bringing a live earthworm into contact with a chloride(s) of a metal(s) selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water, grinding the live earthworm, freeze-drying the resulting ground product, dissolving the thus freeze-dried product in water or an aqueous ethanol solution, and then removing or separating insoluble fractions.

EXAMPLES

The present invention will now be described in more detail by way of examples thereof. The present invention, however, is not restricted by the following examples by any means. It is noted here that, unless otherwise specified, "%" used below is all by mass.

[Preparation of Dry Earthworm Powder]

After leaving 30 kg of live red earthworms (*Lumbricus rubellus*) to stand in a bright place for 24 hours and stripping off dirt adhering to their skin, the live red earthworms were spread at a thickness of about 5 cm on a flat dish and 250 g of sodium chloride was uniformly sprinkled thereon. The earthworms were washed with water 20 minutes thereafter. Then, 15 seconds after sprinkling 250 g of citric acid on the earthworms in the same manner, 30 L of pure water was added thereto for dilution. In this process, the pH of the resulting solution was 2.25 immediately after the addition of water and 2.74 after the completion of the dilution. When sprinkled with the citric acid powder, the earthworms excreted yellow body fluid at once. After the dilution with water, the earthworms were maintained in this state for 20 minutes. Next, the live earthworms were taken out of the resulting dirty aqueous citric acid solution, washed with water and subsequently ground at 10° C. using a homogenizer to prepare an earthworm paste. Then, after subjecting this earthworm paste to vacuum degassing so as to remove the gases contained therein, the earthworm paste was transferred to a stainless-steel. tray where the earthworm paste was instantaneously rapidly cooled to −35° C. and maintained at this temperature for 50 hours to be slowly frozen. The thus frozen earthworm paste was maintained at −35° C. under a pressure of 0 Pa for 2 hours. Thereafter, the earthworm paste was heated and dried at 25° C. under a pressure of 40 Pa for 10 hours, at 40° C. under a pressure of 35 Pa for 14 hours and then at 65° C. under a pressure of 35 Pa for 12 hours and lastly, the resultant was maintained at a temperature of 80° C. and a pressure of 25 Pa for 6 hours, thereby vacuum freeze-drying the earthworm paste. By this treatment, a pale-yellow dry earthworm powder having a water content of 8% by mass was obtained.

The thus obtained dry earthworm powder was heat-treated using a beating apparatus RM-50D (manufactured by Okawara MFG. CO., Ltd.). As for the heating conditions, the dry earthworm powder was heated to 120° C. over a period of 90 minutes, maintained at 120° C. for 20 minutes and then cooled to 40° C. over a period of 240 minutes. Thereafter, the dry earthworm powder was taken out.

The thus heat-treated dry earthworm powder was dissolved in 50% aqueous ethanol solution such that a ratio, ethanol-freeze-dried powder, of 20:1 (v/w) was attained, and the resulting solution was shaken for 1 hour at 1,500 rpm under room temperature (25° C.). Then, the solution was centrifuged for 15 minutes at 4° C. and 10,000×g, and the resulting supernatant was separated and vacuum-concentrated at 75° C. for 15 minutes. This supernatant was transferred to a stainless-steel tray where the supernatant was instantaneously rapidly cooled to −35° C. and maintained at this temperature for 50 hours to be slowly frozen. The thus frozen earthworm paste was maintained at −35° C. under a pressure of 0 Pa for 2 hours. Thereafter, the earthworm paste was heated and dried at 25° C. under a pressure of 40 Pa for 10 hours, at 40° C. under a pressure of 35 Pa for 14 hours and then at 65° C. under a pressure of 35 Pa for 12 hours and lastly, the resultant was maintained, at a temperature of 80° C. and a pressure of 25 Pa for 6 hours, thereby vacuum freeze-drying the earthworm paste to obtain a dry earthworm powder A-1.

[Culturing of Bovine Adrenal Chromaffin Cells]

Bovine adrenal chromatin cells isolated from bovine adrenal medulla were cultured for 48 hours in a culture medium (37° C. Embryologically, adrenal chromaffin cells are derived from neural crest; therefore, they are often utilized as a neuron model.

[Measurement of Catecholamine Secretion]

Figure 1:
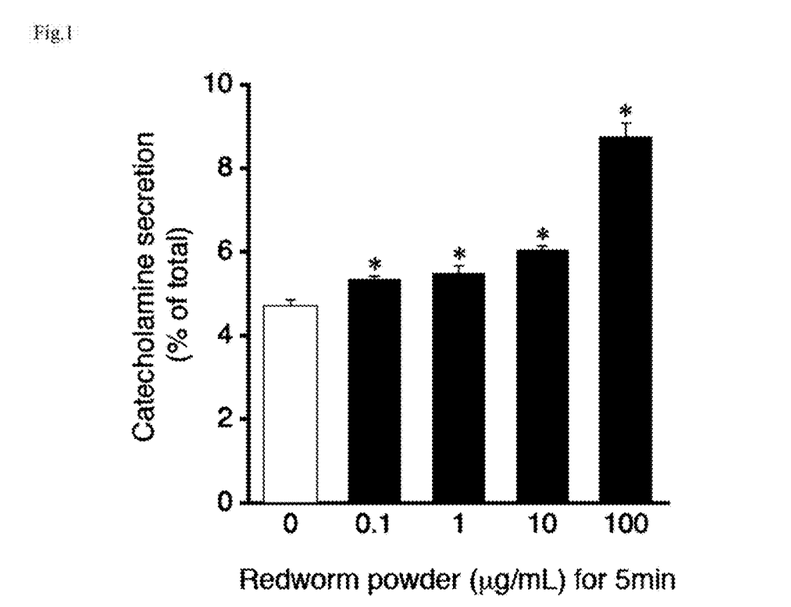
FIG. 1 is a graph showing the changes in the amount of catecholamine secretion of bovine adrenal chromaffin cells caused by incorporation of a dry earthworm powder. The abscissa represents the concentration of the dry earthworm powder. The ordinate represents the amount of the catecholamine secretion. The amount of the intracellular catecholamine after 5 minutes of culturing at a dry earthworm powder concentration of 0 μg/mL was taken as 100%.

The culture medium of the thus cultured bovine adrenal chromaffin cells ($4\times10^6$ cells: 35-mm dish) was substituted with 1 mL of KRP solution (Krebs-Ringer phosphate buffer) in which the dry earthworm powder A-1 obtained above had been dissolved at a concentration of 0. 0.1, 1, 10 or 100 μg/m and the resultants were cultured at 37° C. for 5 minutes. From each KRP solution used for this culturing in which the dry earth powder was dissolved, only the solution was recovered in an amount of 0.1 mL, and 0.1 mL of 0.2N perchloric acid and 0.2 mL of 3,4-dihydroxybenzylamine (DHBA) were added thereto so as to determine the amount of catecholamine secretion using HPLC (high-performance liquid chromatography) and COULOCHEM II manufactured by ESA (electrochemical detector). FIG. 1 shows the results of calculating the amount of catecholamine secretion, taking the amount of catecholamine in the bovine adrenal chromaffin cells ($4\times10^6$ cells) that were cultured at 37° C. for 5 minutes with 0 μg/mL of the dry earthworm powder A-1 as 100%.

[Measurement of Intracellular Calcium Concentration]

Figure 2:
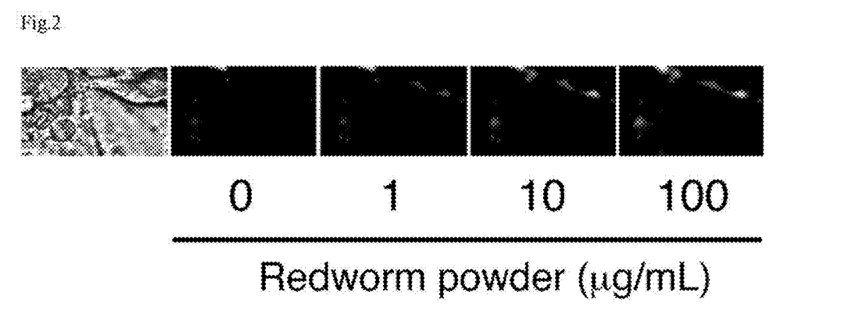
FIG. 2 provides photographs showing the changes in the intracellular calcium concentration of bovine adrenal chromaffin cells caused by incorporation of a dry earthworm powder.
Figure 3:
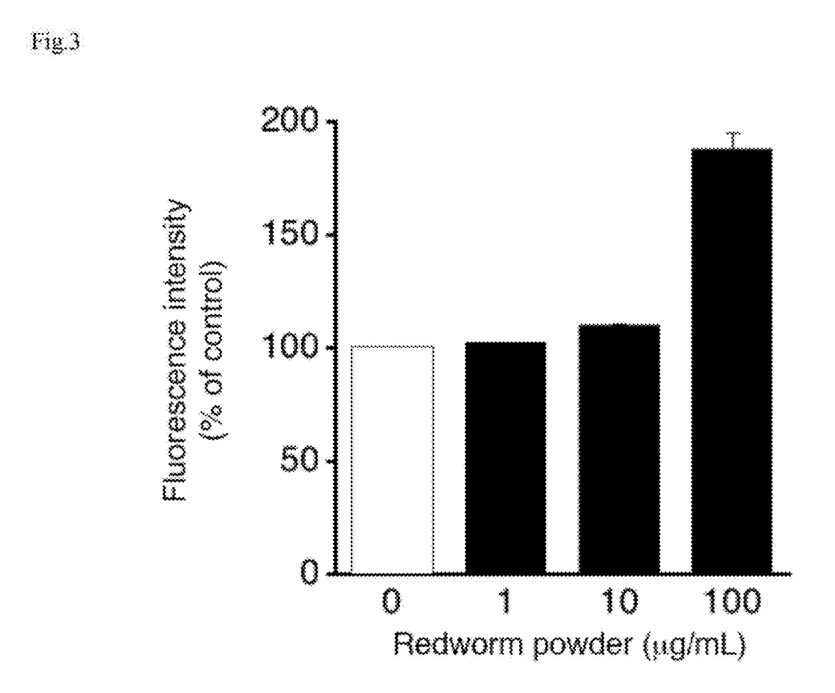
FIG. 3 is a graph showing the changes in the fluorescence intensity of intracellular calcium of bovine adrenal chromaffin cells caused by incorporation of a dry earthworm powder. The abscissa represents the concentration of the dry earthworm powder. The ordinate represents the fluorescence intensity. The fluorescence intensity of cells cultured at a dry earthworm powder concentration of 0 μg/mL was taken as 100%.

The culture medium of the bovine adrenal chromaffin cells cultured in the above ($4\times10^6$ cells: 35-mm dish) was substituted with 1 mL of KRP solution to which Fluo-4-AM manufactured by Dojindo Laboratories, Ltd. had been added at a final concentration of 5 μmol/mL, and the resultant was cultured at 37° C. for 30 minutes. Thereafter, the culture dish was fixed on a reflux apparatus under a fluorescence microscope and refluxed with KRP solutions in each of which the dry earthworm powder A-1 obtained above had been dissolved at a concentration of 0, 1, 1.0 or 100 μg/mL. Photographs of each culture dish were taken at 5-second intervals from the start of the reflux and the fluorescence intensity of the entire photograph at the fluorescence intensity peak (488 nm) was measured. FIG. 2 shows the photographs taken at the fluorescence intensity peak, and FIG. 3 shows the results of comparing the thus measured fluorescence intensities, taking the fluorescence intensity determined at its peak for the culture refluxed with 0 μg/mL of the dry earthworm powder A-1 as 100%.

It is noted here that, in adrenal chromaffin cells and nerve cells, an increase in the intracellular calcium concentration is known to facilitate the priming of catecholamine-containing secretory vesicles (membrane fusion of secretory vesicles) and to thereby induce catecholamine secretion.

[Phosphorylation of Tyrosine Hydroxylase]

Figure 4:
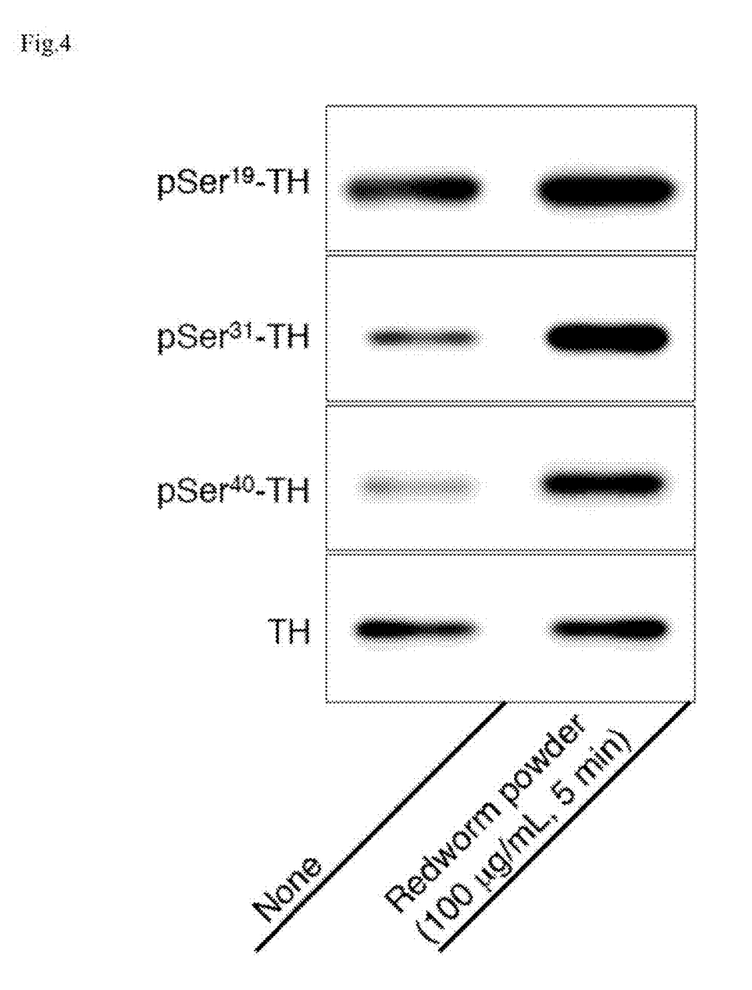
FIG. 4 provides photographs showing the results of Western blot performed to investigate the changes in the phosphorylation of tyrosine hydroxylase in bovine adrenal chromaffin cells caused by incorporation of a dry earthworm powder.

The culture medium of the bovine adrenal chromaffin cells cultured in the above ($4\times10^6$ cells: 35-mm dish) was substituted with 1 mL of KRP solution (Krebs-Ringer phosphate buffer) in which the dry earthworm powder A-1 obtained above had been dissolved at a concentration of 0 or 100 μg/mL, and the resultants were cultured at 37° C. for 5 minutes. Then, after washing the cells with PBS(−) solution (4° C.), only the cells ($4\times10^6$ cells) were promptly recovered and phosphorylation of tyrosine hydroxylase (TH) was detected by Western blotting. The results thereof are shown in FIG. 4.

It is noted here that tyrosine hydroxylase is a rate-limiting enzyme for biosynthesis of catecholamines and an increase in the intracellular calcium concentration causes phosphorylation and activation of tyrosine hydroxylase.

As clearly seen from FIG. 1, as compared to the control (KRP solution containing no dry earthworm powder), the dry earthworm powder significantly increased the catecholamine secretion by 85% at a concentration of 100 μg/mL. As clearly seen from FIGS. 2 and 3, the dry earthworm powder also increased the intracellular calcium as compared to the control. From FIG. 4, it is apparent that the dry earthworm powder enhanced phosphorylation (pSer-TH) of the serine residues (the 19th, 31st and 40th serine residues) of tyrosine hydroxylase, which is a rate-limiting enzyme for biosynthesis of catecholamines, and this resulted in an increase in the tyrosine hydroxylase activity.

The invention claimed is:

1. A method of promoting catecholamine production, said method comprising the use of a catecholamine production accelerator comprising a dry powder, ground product and/or extract of an earthworm,
wherein the dry powder, ground product and/or extract of an earthworm is prepared by a method comprising the steps of:
bringing a live earthworm into contact with a chloride of at least one metal selected from the group consisting of potassium, sodium, magnesium and calcium; and
subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water, grinding the live earthworm and then freeze-drying the thus obtained ground product.

2. A method of promoting catecholamine production, said method comprising the use of a catecholamine production accelerator comprising a dry powder, ground product and/or extract of an earthworm, wherein the dry powder, ground product and/or extract of an earthworm is prepared by a method comprising the steps of:

bringing a live earthworm into contact with a chloride(s) of a metal(s) selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water, grinding the live earthworm and then freeze-drying the thus obtained ground product.

3. A method of treating or preventing a disease caused by catecholamine deficiency, said method comprising administration of a dry powder, ground product and/or extract of an earthworm to a subject in an effective dose, wherein the dry powder, ground product and/or extract of an earthworm is prepared by a method comprising the steps of:

bringing a live earthworm into contact with a chloride of at least one metal selected from the group consisting of potassium, sodium, magnesium and calcium; and subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water, grinding the live earthworm and then freeze-drying the thus obtained ground product.

4. The method according to claim 3, wherein said disease caused by catecholamine deficiency is selected from the group consisting of Alzheimer's disease and Parkinson's disease.

5. A method of treating or preventing a disease caused by catecholamine deficiency, said method comprising administration of a dry powder, ground product and/or extract of an earthworm to a subject in an effective dose, wherein the dry powder, ground product and/or extract of an earthworm is prepared by a method comprising the steps of:

bringing a live earthworm into contact with a chloride(s) of a metal(s) selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water, grinding the live earthworm and then freeze-drying the thus obtained ground product.

6. The method according to claim 5, wherein said disease caused by catecholamine deficiency is selected from the group consisting of Alzheimer's disease and Parkinson's disease.

* * * * *